United States Patent [19]

Fischer et al.

[11] Patent Number: 4,804,542
[45] Date of Patent: Feb. 14, 1989

[54] GELATIN CAPSULES AND METHOD OF PREPARING SAME

[75] Inventors: Gerhard Fischer, Eberbach/Baden; Benedikt Schneider, Backnang; Helmut Jahn, Stuttgart, all of Fed. Rep. of Germany

[73] Assignee: R. P. Scherer GmbH, Fed. Rep. of Germany

[21] Appl. No.: 36,311

[22] Filed: Apr. 9, 1987

[30] Foreign Application Priority Data

Aug. 20, 1985 [DE] Fed. Rep. of Germany .. 35 29 694

[51] Int. Cl.$^4$ ............................................... A61K 9/64
[52] U.S. Cl. .................................... 424/456; 424/455; 424/457

[58] Field of Search ................... 424/455, 457, 456

[56] References Cited

U.S. PATENT DOCUMENTS

| | | | |
|---|---|---|---|
| 3,126,321 | 3/1964 | Kurtz | 424/455 |
| 3,427,378 | 2/1969 | Henderson et al. | 424/457 |
| 4,198,391 | 4/1980 | Grainger | 424/455 |

Primary Examiner—Thurman K. Page
Assistant Examiner—J. R. Horne
Attorney, Agent, or Firm—Wegner & Bretschneider

[57] ABSTRACT

Gelatin capsules, consisting of a capsule sheath and a capsule filling, the capsule sheath consisting of gelatin, optionally a plasticizer and further additives, and the capsule filling containing active substances and/or dietectic agents and, optionally, further additives and a liquid or powder, in the capsule sheath additionally contain an additive of at least 1% by weight of an agent which in the pure state is capable of absorbing water in an amount of at least 10% by weight of its own weight without undergoing a change in its appearance.

10 Claims, No Drawings

GELATIN CAPSULES AND METHOD OF PREPARING SAME

The present invention relates to gelatin capsules consisting of a capsule sheath and a capsule filling, the capsule sheath consisting of gelatin, optionally a plasticizer and further additives, and the capsule filling containing active substances and/or dietetic agents and, optionally, further additives and a liquid or powder. The present invention further relates to a method for preparing such gelatin capsules.

BACKGROUND OF THE INVENTION

The preparation of soft gelatin capsules has been extensively described, e.g., in Lachmann, Theory and Practice of Industrial Pharmacy, Lea and Febiger, Philadelphia, 2nd Edition. Therein it has been set forth that the type of the soft capsule filling materials is substantially restricted to three categories, namely water-immiscible, non-volatile or readily volatile carriers such as oils, fats, ethereal oils, chlorinated hydrocarbons, esters, ethers, higher alcohols and organic acids. Thus, this category of auxiliary and active ingredients is relatively easy to encapsulate and allows a rather wide margin for formulating the capsule sheath.

The second category comprises water-miscible non-volatile materials such as polyethylene glycols or emulsifiers. This category is much more difficult to process. Thus, the DE-OS No. 33 07 353, e.g., describes a process for preparing polyethyleneglycol-containing soft gelatin capsules, according to which process polyethyleneglycol can be reliably encapsulated only if quite well-defined parameters are maintained with respect to the capsule sheath as well as to the capsule fill material. The problems encountered in encapsulating may be explained by that polyethyleneglycol-containing fillings will strongly interact with the capsule sheath and thus, the storage stability of the capsules is n longer readily ensured.

Finally, the third category comprises water-miscible and relatively low-volatile components such as, e.g., glycerol, propyleneglycol or benzyl alcohol. In this category the interactions described in the category (2) are so strong that components of the last category can only be encapsulated in concentrations of up to a maximum of 10%.

Rated to be not capable of being subjected to encapsulation, according to Lachmann, loc. cit., are liquids comprising more than 5% of water and lower molecular weight organic water-soluble compounds, more particularly lower alcohols such as ethyl alcohol, ketones and amines.

Particular problems are also involved in processing water-soluble or hygroscopic active substances in gelatin capsules, since these also adversely affect the capsule wall.

SUMMARY OF THE INVENTION

It is the object of the present invention to encapsulate this third group of substances which so far could not be encapsulated at all, i.e to prepare capsule fillings which contain at least one water-miscible, water-soluble, water-sensitive or hydrophilic readily volatile material. It is another object of the present invention, more easily to encapsulate substances of the second category which so far could only be encapsulated with difficulties.

It was surprisingly found that said object can be attained by adding, as an additive to the capsule sheath, at least 1% by weight of an agent which in the pure state is capable of absorbing water in an amount of at least 10% by weight of its own weight.

These materials, more particularly, include starches, starch derivatives, celluloses, cellulose derivatives, milk powder, non-hygroscopic mono-, di- and oligosaccharides, magnesium trisilicate and silicon dioxide as well as mixtures thereof.

By using these additives to the capsule sheath according to the invention it has for the first time been possible to employ capsule fillings which contain one or more substances selected from the group comprising the lower alcohols, ethers, esters, alkanals, alkanones, polyols or amines. As used herein, the word "lower" refers to a compound of 6 carbon atoms or less. Furthermore, it has been possible according to the invention to prepare capsule fillings containing one or more materials selected from the group comprising concentrated aqueous sugar solutions, starch syrups, hydrogenated starch syrups, sugar derivative solutions and honey. Finally it is possible without problems to encapsulate substances only difficult to encapsulate such as water-miscible non-volatile materials, e.g., polyethylene glycols or emulsifiers.

Of particular importance are soft gelatin capsules such as those specifically used in the pharmaceutical sector and which are allowed to be swallowed unchewed. However, according to the present invention there can also be prepared soft chewable capsules which, more specifically, may be employed in the food and dietetic area. However, basically it is also possible by, using the additives to the capsule sheath according to the invention, to prepare stable hard gelatin capsules which are storage-stable in spite of their unusual capsule fillings.

DETAILED DESCRIPTION OF THE INVENTION

Thus, the subject matter of the present invention comprises gelatin capsules consisting of
  (a) a capsule sheath and
  (b) a capsule filling,
the capsule sheath consisting of gelatin, optionally a plasticizer and further additives, and the capsule filling containing active substances and/or dietetic agents and, optionally, further additives and a liquid or powder, characterized in that
  (a) the capsule sheath contains, as an additive, at least 1% by weight of an agent which in the pure state is capable of absorbing water in an amount of at least 10% by weight of its own weight without undergoing a change in its external appearance and
  (b) the capsule filling contains at least one water-miscible water-soluble, water-sensitive or hydrophilic readily volatile material.

Another subject matter of the present invention comprises a method for preparing such gelatin capsules, more specifically soft gelatin capsules consisting of
  (a) a capsule sheath and
  (b) a capsule filling,
the capsule sheath consisting of gelatin, optionally a plasticizer and further additives, and the capsule filling containing active substances and/or dietetic agents and, optionally, further additives and a liquid or powder, in a per se known manner, characterized in that (a) to the gelatin decoction there is added, as an additive, a suspension or solution of an agent which in the pure state is capable of absorbing water in an amount of at least 10% by weight of its own weight without undergoing a change in its appearance and (b) as the capsule filling there is employed at least one water-miscible water-soluble, water-sensitive or hydrophilic readily volatile material.

A further subject matter of the present invention comprises a method for preparing gelatin capsules consisting of (a) a capsule sheath and
(b) a capsule filling, the capsule sheath consisting of gelatin, optionally a plasticizer and further additives, and the capsule filling containing active substances and/or dietetic agents and, optionally, further additives and a liquid or powder, in a per se known manner, characterized in that (a) to the gelatin decoction there is added, as an additive, a suspension or solution of an agent which in the pure state is capable of absorbing water in an amount of at least 10% by weight of its own weight without undergoing a change in its external appearance and (b) the capsule filling contains one or more substances selected from the group comprising vegetable oils, semi-synthetic or synthetic oils, fatty derivatives, animal fats or oils, lecithins and/or pharmaceutically usable emulsifiers.

So far it has remained unclear, why and how the addition according to the invention of agents, which in the pure state are capable of absorbing water in an amount of at least 10% by weight of their own weight without undergoing a change in appearance, modifies the properties to such an extent that now capsule fillings can be employed which so far were believed to be not at all suitable for being encapsulated.

The selection and concentration of such agent to some degree depend on the intended specific capsule filling. Also the way of incorporating said agents into the gelatin sheath to some degree depends on the product. Nevertheless, all of the results obtained so far are in favour of the conclusion of that by the mere addition of said agents it has become possible successfully to render the capsule sheath inert to influences exerted by the capsule filling and by the environment and to reduce the permeability for all water-soluble, hydrophilic and readily volatile materials. It is quite astonishing that these agents when being processed can be added to the gelatin decoction either as a dispersion or even as a solution. i.e. in a form in which, due to the large amount of water, they would indeed be capable of undergoing a change in appearance. In the final capsule sheath they seem to exert some kind of buffering effect on the water contents of the sheath and of the capsule filling, while, however, such effect is not capable of providing an explanation for why hereby according to the invention there are formed stable and usable capsules.

The additives to be added to the capsule sheaths according to the invention may be selected from the most varied materials. First, starches and starch derivatives as well as celluloses and cellulose derivatives have proven to be particularly valuable. Thus, these include native potato, corn, wheat or tapioca starch. As starch derivatives there may be considered physically treated modified starches, oxidized, hydrolyzed, enzyme-treated, cross-linked, esterified or etherified starches. As the cellulose there is usable, more particularly, microcrystalline cellulose, and so are cellulose derivatives which meet the requirements according to the invention with respect to the behavior to water.

Unexpectedly, non-hygroscopic mono-, di- and oligo-saccharides are also suitable. Lactose may be employed in the pure state as well as in the form of milk powder. However, inorganic materials such as magnesium trisilicate and colloidal silicon dioxide also serve the purpose of the invention.

Some of these materials are capable of absorbing substantially more than 10% by weight, based on their own weight, of water without undergoing a change in appearance. Other agents of this group are evenly dissolved by larger amounts of water. Nevertheless they fulfill the condition according to the invention relating to the improvement of the capsule sheath.

For carrying out the method according to the invention for preparing gelatin capsules the agents are added to the gelatin decoction in the form of suspension or solution. Upon conventional filling and drying of the capsules there result directly usable products, even in the case that they have been filled with substances so far thought to be not suitable for encapsulation.

For example, one substance rated to cause serious problems has been ethanol. Conventional soft gelatin capsules prepared in accordance with prior art allow ethanol to be diffused through the capsule wall immediately after drying, so that the capsules continuously are losing weight and shape and do not fully dry up any more. With other water-miscible, water-soluble or water-sensitive substances it was not possible according to prior art to avod diffusing of water into the capsule filling or diffusing of the capsule filling into the capsule sheath.

Both phenomena resulted in the formation of qualitatively unacceptable products. It is astonishing that this undesired interaction between capsule sheath and capsule filling is suppressed by the addition of the above-described agents to such an extent that stable and storable capsules are formed. For example, readily water-soluble or hygroscopic medicaments previously extracted so much residual water from the gelatin sheath that the latter became brittle. In soft gelatin capsules this embrittlement could be halted to some degree by addition of larger amounts of selected plasticizers to the gelatin sheath. However, in hard gelatin capsules containing no such plasticizer in the sheath, such a compensation is not possible. Thus, by the addition according to the invention of the agents mentioned hereinabove it has also become possible to stably fill hygroscopic medicaments into hard gelatin capsules.

In contrast thereto, in soft gelatin capsules substances with high solubility in water have always led to the result that they diffused from the capsule filling into the capsule sheath and thereby impaired the stability and quality of the capsule sheath. Even when the capsules have been dried up, that diffusion process may continue to proceed, so that after some time an absolutely unacceptable accumulation of the active ingredients within the gelatin sheath will have taken place. Then, this resulted in the gelatin sheath thereafter becoming soft again or in extreme cases the capsules even suffered breaks at the fuse seam. According to the present invention, all of these undesirable interactions surprisingly can be eliminated or suppressed to such a high degree that they no longer create any trouble.

The interaction between the capsule sheath and environment is also significantly reduced by use of the present invention. Thus, capsules in general are stable for long-term storage only at 15° C. to 25° C. at a relative humidity of 60%, since due to absorption of moisture from the air the capsules become soft and/or begin to adhere to one another. The capsules of the invention are by far less sensitive to becoming soft and tacky and sticking together, which phenomenon could be explained in terms of reduced water uptake from the environment.

It has further been found that it is possible to prepare capsule sheaths useful for the purposes of the invention even in the case that they contain at least 50% by weight of non-hygroscopic sugars and, as a capsule filling to fill into said sheaths, a dietetic food product, a food product, a cosmetic or a physiologically compatible technical auxiliary material. Capsule sheaths containing at least 50% by weight of a non-hygroscopic sugar, regardless of the filling, fall within the definition range of sugar products and, thus, may be dyed with colors allowed under the food law. If sorbitol is used, such capsule sheath even meets the definition of dietetic food materials. Thus, such capsules may be filled with a good product or a food material. Furthermore it is also possible to fill such capsule sheaths with a cosmetic or a physiologically compatible additive and to offer it in the form of capsules.

Typical embodiments of the gelatin capsules according to the present invention and methods for preparing same are illustrated in the following examples.

EXAMPLE 1

A gelatin decoction is prepared in a per se known manner from 48 kg of gelatin, 16 kg of glycerol and 36 kg water. To this decoction there is added a homogeneous trituration of 20 kg of corn starch in 20 kg of glycerol. Therefrom gelatin capsules were made which were filled with pure glycerol.

For comparison an identical formulation was prepared, however without the addition of corn starch. The formulation according to the invention was unobjectionably processable, exhibited a solid gelatin sheath and was storage stable, whereas the comparative formulation was already deformed after processing, remained soft and tacky and was not further processable.

EXAMPLE 2

The same recipe as in Example (1) was filled with propylene carbonate. For comparison again a formulation was prepared without an addition of corn starch. Again it showed that the gelatin capsules according to the invention could be processed without objections or defects, had a solid gelatin sheath and were storage stable, whereas the Comparative Example was already deformed immediately after processing, was soft and tacky and could not be further processed.

EXAMPLES 3 and 4

The same recipe as in Example (1) was filled with a mixture comprising equal portions of polyethyleneglycol 400 and ethyl alcohol and also a mixture of equal portions of propanediol and ethyl alcohol.

Again the recipes according to the invention were unobjectionably processable and yielded storage stable solid products, whereas the Comparative Examples without the addition of cornstarch were deformed already immediately after processing, remained soft and tacky and, thus, could not be further processed.

EXAMPLES 5 and 6

From 5 kg of sugar, 3.8 kg of glucose syrup, 0.4 kg of a 70% aqueous sorbitol solution, 6 kg of a potato starch acetate providing a low-viscosity material upon boiling and 5.8 kg of water there was prepared a solution which was stirred into 60 kg of a gelatin decoction consisting of 46% of gelatin, 19.8% of glycerol and 34.2% of water.

Into this material used for the capsule sheath there was filled a 70% aqueous sorbitol/sorbitan solution or a mixture comprising 80% of glucose syrup, 10% of glycerol and 10% of water. There were formed stable soft chewable capsules. For comparison, the same gelatin decoction was prepared without potato starch acetate and sugar additions. Again there could be determined that the gelatin without the additives was not stable in shape.

EXAMPLE 7

A gelatin decoction was prepared in Example (1) from 48 kg of gelatin, 16 kg of glycerol and 36 kg water. To this decoction there was added a trituration of 28 kg of skim milk powder, 48 kg of glycerol and 16 kg of water. Therefrom capsules were made which contained a solution of 250 mg of choral hydrate in 173 mg of polyethyleneglycol 400 per capsule.

In contrast to the Comparison Example without skim milk powder, the gelatin sheath was still so hard that even upon the action of smooth pressure no deformation of the gelatin sheath occurred.

EXAMPLE 8

A gelatin decoction was prepared in Example (1) from 48 kg of gelatin, 16 kg of glycerol and 36 kg water. To this decoction there was added a homogeneous trituration of 10 kg of microcrystalline cellulose and 14 kg of glycerol. Therefrom, soft gelatin capsules were made which contained a filling of 85% of honey and 15% of glycerol. There resulted solid and storage stable gelatin capsules the quality of which was unobjectionable.

EXAMPLE 9

A gelatin decoction was prepared from 33 kg of gelatin and 61 kg of glycerol. To this decoction there was added a solution of 5 kg of starch acetate in 5 kg of water. This gelatin decoction was further processed in conventional manner to give hard gelatin oapsules. Into these capsules there was filled a mixture comprising 60% of choline chloride, 10% of lactose, 19% of corn starch and 1% of magnesium stearate. In contrast to the Comparison Example without starch acetate the capsule sheath does not embrittle.

EXAMPLE 10

A gelatin decoction was prepared by heating 17.5 kg of gelatin, 6.93 kg of 85% glycerol and 12.32 kg water. This was admixed with 25 kg of a heated solution consisting of 10.53 kg of crystal sugar (saccharose), 13.16 kg of an 80% glucose syrup and 1.31 kg of water. This mixture could be processed into capsule sheaths in a per se known manner.

Into these capsule sheaths there were filled vitaminized aqueous solutions of fondant (water content 25%). Chewable capsules having good chewing properties and, depending on the degree of drying, pasty or nearly solid contents were formed. Furthermore they were filled with an aromatized aqueous sorbitol solution (water content 20%). There were formed oval elastic well chewable bodies with liquid contents.

Finally, said capsule sheaths were filled with honey and with honey containing a ribwort extract. Well chewable honey capsules were obtained.

What is claimed is:

1. A gelatin capsule comprising
   a capsule sheath and
   a capsule filling, wherein
   said sheath contains a gelatin and at least 1% by weight of an agent selected from the group consisting of starches, starch derivatives, celluloses, cellulose derivatives, milk powder, nonhygroscopic mono-, di- and oligosaccharides, magnesium trisilicate and silicon dioxide, which agent is capable of absorbing water in an amount of at least 10% by weight of its own weight without undergoing a change in its external appearance, and
   said filling contains at least one water-miscible, water-soluble, water-sensitive or hydrophilic, readily volatile material.

2. Gelatin capsule of claim 1, wherein the capsule filling contains one or more materials selected from the group consisting of lower alchohols, ethers, esters, alkanals, alkanones, polyols and amines.

3. Gelatin capsule of claim 1, wherein the capsule filling contains one or more materials selected from the group consisting of lower alcohols, ethers, esters, alkanals, alkanones, polyols and amines.

4. Gelatin capsule of claim 1, wherein the capsule filling contains one or more materials selected from the group consisting of concentrated aqueous sugar solutions, starch syrups, hydrogenated starch syrups, sugar derivative solutions and honey.

5. Gelatin capsule of claim 1, wherein the capsule filling contains one or more materials selected from the group consisting of concentrated aqueous sugar solutions, starch syrups, hydrogenated starch syrups, sugar derivative solutions and honey.

6. Gelatin capsule of claim 1 wherein the capsule sheath is one of a soft gelatin capsule.

7. Gelatin capsule of claim 1 wherein the capsule sheath is one of a soft chewable capsule.

8. Gelatin capsule of claim 1 wherein the capsule sheath contains at least 50% by weight of non-hygroscopic sugars and the capsule filling is a food material, a cosmetic or a physiologically compatible additive material.

9. Gelatin capsule of claim 1, wherein the capsule sheath further contains a plasticizer.

10. Gelatin capsule of claim 1, wherein said capsule filling is a food material, a cosmetic, or a bio-affecting material.

* * * * *